US011819494B2

(12) United States Patent
Dalsgaard et al.

(10) Patent No.: US 11,819,494 B2
(45) Date of Patent: Nov. 21, 2023

(54) TREATMENT OF IDIOPATHIC PULMONARY FIBROSIS

(71) Applicant: VICORE PHARMA AB, Stockholm (SE)

(72) Inventors: Carl-Johan Dalsgaard, Stockholm (SE); Rohit Batta, Stockholm (SE)

(73) Assignee: VICORE PHARMA AB, Stockholm (SE)

( * ) Notice: Subject to any disclaimer, the term of this patent is extended or adjusted under 35 U.S.C. 154(b) by 0 days.

(21) Appl. No.: 17/680,654

(22) Filed: Feb. 25, 2022

(65) Prior Publication Data

US 2023/0248698 A1    Aug. 10, 2023

(30) Foreign Application Priority Data

Feb. 10, 2022   (GB) ..................................... 2201723

(51) Int. Cl.
*A61K 31/4178*    (2006.01)
*A61K 9/48*    (2006.01)
*A61P 11/00*    (2006.01)
*A61P 1/00*    (2006.01)

(52) U.S. Cl.
CPC .......... *A61K 31/4178* (2013.01); *A61K 9/485* (2013.01); *A61K 9/4858* (2013.01); *A61P 1/00* (2018.01)

(58) Field of Classification Search
CPC .. A61K 31/4178; A61K 9/485; A61K 9/4858; A61P 11/00
See application file for complete search history.

(56) References Cited

U.S. PATENT DOCUMENTS

| | | |
|---|---|---|
| 2003/0113330 A1 | 6/2003 | Uhal |
| 2012/0035232 A1 | 2/2012 | Stecklings et al. |
| 2016/0074466 A1 | 3/2016 | Franklin et al. |
| 2018/0078529 A1 | 3/2018 | Dahlof et al. |

FOREIGN PATENT DOCUMENTS

| | | | |
|---|---|---|---|
| EP | 2832357 A1 | 2/2015 | |
| WO | 99/043339 A1 | 9/1999 | |
| WO | 2002/096883 A1 | 12/2002 | |
| WO | WO-2005123072 A1 * | 12/2005 | ........... A61K 31/135 |
| WO | 2016/139475 A1 | 9/2016 | |
| WO | 2021/214488 A1 | 10/2021 | |
| WO | WO-2021214486 A1 * | 10/2021 | ............... A61K 9/48 |
| WO | WO-2021214487 A1 * | 10/2021 | |

OTHER PUBLICATIONS

Horiba Scientific. A Guidebook to Particle Size Analysis. 2017. 34 pages. (Year: 2017).*

International Search Report and Written Opinion for corresponding Application No. PCT/GB2015/050552 (dated Jun. 29, 2016).
Wan et al., "Design, Synthesis, and Biological Evaluation of the First Selective Nonpeptide AT 2 Receptor Agonist," J. Med. Chem. 47(24):5995-6008 (2004).
Parra et al., "Angiotensin II Type 1 and 2 Receptors and Lymphatic Vessels Systemic Sclerosis and Idiopathic Pulmonary Fibrosis," Clinics 69(1):47-54 (2014).
Nabeshima et al., "Anti-Fibrogenic Function of Angiotensin II Type 2 Receptor in CC14-Induced Liver Fibrosis," Biochem. Biophys. Res. Comm. 346(3):658-664 (2006).
Bruce et al., "Selective Activation of Angiotensin AT 2 Receptors Attenuates Progression of Pulmonary Hypertension and Inhibits Cardiopulmonary Fibrosis," British J. Pharmacol. 172(9):2219-2231 (2015).
De Gasparo et al., "International Union of Pharmacology. XXIII. The Angiotensin II Receptors," Pharmacol. Rev. 52:415-472 (2000).
King et al., "Idiopathic Pulmonary Fibrosis," Lancet 378:1949-1961 (2011).
King et al., "A Phase 3 Trial of Pirfenidone in Patients with Idiopathic Pulmonary Fibrosis," N. Engl. J. Med. 370:2083-2092 (2014).
Ley et al., "Clinical Course and Prediction of Survival in Idiopathic Pulmonary Fibrosis," Am. J. Respir. Crit. Care Med. 183:431-440 (2011).
Noble, "Pulmonary Fibrosis: Patterns and Perpetrators," J. Clin. Invest. 122:2756-2762 (2012).
Rafii et al., "A Review of Current and Novel Therapies for Idiopathic Pulmonary Fibrosis," J. Thorac. Dis 5:48-73 (2013).
Richeldi et al., "Efficacy and Safety of Nintedanib in Idiopathic Pulmonary Fibrosis," N. Engl. J. Med. 370:2071-2082 (2014).
Non-confidential Disclosure Materials, presented by inventor Björn Dahlöf to Sunstone Capital A/S in Copenhagen, Denmark (Dec. 13, 2013).
Non-Final Office Action in U.S. Appl. No. 15/554,213, dated Jan. 11, 2018.
Maher and Strek, "Antifibrotic Therapy for Idiopathicpulmonary Fibrosis: Time to Treat," Respiratory Research 20:205 (2019).
Isshiki et al., "Incidence of Acute Exacerbation of Idiopathic Pulmonary Fibrosisin Patients Receiving Antifibroticagents: Real-world Experience," Respiratory Medicine 187:106551 (2021).
Mei et al., "Activation of Angiotensin II Type-2 Receptor Protects Against Cigarette Smoke-induced COPD," Pharm. Res., 161:105223 (2020).

(Continued)

*Primary Examiner* — Shirley V Gembeh
*Assistant Examiner* — Olga V. Tcherkasskaya
(74) *Attorney, Agent, or Firm* — Troutman Pepper Hamilton Sanders LLP (Rochester)

(57) ABSTRACT

According to the invention there is provided a method of improving (e.g. restoring) function in a patient having idiopathic pulmonary fibrosis, which method comprises perorally administering a therapeutically-effective amount of N-butyloxycarbonyl-3-(4-imidazol-1-ylmethylphenyl)-5-iso-butylthiophene-2-sulfonamide (C21), or a pharmaceutically acceptable salt thereof, to said patient. Said treatment is capable of treating said IPF in a therapeutic, including a curative, fashion.

19 Claims, 1 Drawing Sheet

(56) References Cited

OTHER PUBLICATIONS

Rathinasabapathy et al., "The Selective Angiotensin II Type 2 Receptor Agonist, Compound 21, Attenuates the Progression of LungFibrosis and Pulmonary Hypertensionin an Experimental Model of Bleomycin-Induced Lung Injury," Front. Physiol., 9:180 (2018).
Nathan et al., "Inhaled Treprostinil and Forced Vital Capacity in Patients With Interstitial Lung Disease and Associated Pulmonary Hypertension: A Post-hoc Analysis of the INCREASE Study," Lancet Respir. Med., 9:1266 (2021).
Menk et al., "Angiotensin II Type 2 Receptor Agonist Compound 21 Attenuates Pulmonary Inflammation in a Model of Acute Lung Injury," J. Inflamm. Res., 11:169-178 (2018).
Sumners et al., "Anti-fibrotic Mechanisms of Angiotensin AT2-Receptor Stimulation," Acta Physiologica, 227:e1328 (2019).
Pareto Securities AB Equity Research, "Vicore Pharma Holding AB Newsflash—Interim IPF Phase 2 Data: Unprecedented Among Competitors?" (Feb. 14, 2022).
Flaherty et al., "Stability or Improvement in Forced Vitalcapacity With Nintedanib in Patients With Idiopathic Pulmonary Fibrosis," Eur Respir J 52:1702593 (2018).
Nalbandyan et al., "Compound 21 (C21), a Selective Angiotensin Type 2 (AT2) Receptor Agonist Attenuates Bleomycin Induced Alveolar Epithelial Cell Death," The FASEB Journal 32(S1):829.7 (2018) (Abstract Only).
Batta R. et al., "Investigating the Effects of Stimulating the Angiotensin II Type 2 Receptor (AT2R) on Lung Function in Patients with Idiopathic Pulmonary Fibrosis (IPF)—Design of the Single Arm Open Label AIR Study (AT2R Agonist for Idiopathic Pulmonary Fibrosis to Relieve Impaired Lung Function)," Am. J. Respir. Crit. Care Med. 201:A2263 (2020), American Thoracic Society 2020 International Conference, A63. Mediators of Lung Fibrosis (Abstract Only).
Press Release, "Vicore Pharma Recruits the First Patient in the Phase II Proof-of-Concept Study in Idiopathic Pulmonary Fibrosis," Gothenburg, Nov. 16, 2020.
Cao et al. "Acute Exacerbation of Idiopathic Pulmonary Fibrosis: Usual Interstitial Pneumonitis vs. Possible Usual Interstitial Pneumonitis Pattern," Chinese Medical Journal 132(18):2177-2184 (2019).
Bratt et al., "Predicting Usual Interstitial Pneumonia Histopathology From Chest CT Imaging With Deep Learning," Chest 162(4):815-823 (2022).
Guidance for Industry, "Food-Effect Bioavailability and Fed Bioequivalence Studies," U.S. Department of Health and Human Services, Food and Drug Administration, Center for Drug Evaluation and Research (CDER) Dec. 2002.
Raghu et al. "Diagnosis of Idiopathic Pulmonary Fibrosis," American Journal of Respiratory and Critical Care Medicine 198(5):e44-e68 (2018).
Lynch et al., "Diagnostic Criteria for Idiopathic Pulmonay Fibrosis: A fleischner Society White Paper," Lancet Respir Med 6(2):138-153 (2018).
Decision of Rejection for Japan Application No. 2022-540547, dated May 30, 2023 (English Translation).
O.R.L. Tokyo 45(4):292-295 (2002) (with English Translation).
J. Okayama Med. Assoc. 127:245-249 (2015) (with English Translation).
Drug Delivery System 25(4):384-391 (2010) (with English Translation).
ClinicalTrials.gov ID. NCT04533022, "Safety, Efficacy and Pharmacokinetics of C21 in Subjects With IPF," National Library of Medicine, Bethesda, MD (updated Jun. 9, 2023; first posted Aug. 31, 2020).

* cited by examiner

TREATMENT OF IDIOPATHIC PULMONARY FIBROSIS

This application claims the priority benefit of GB Application No. 2201723.0, filed Feb. 10, 2022, under 35 U.S.C. § 119.

FIELD OF THE INVENTION

This invention relates to new use of a known pharmaceutically-active compound, in particular a new, curative therapeutic treatment of idiopathic pulmonary fibrosis.

BACKGROUND AND PRIOR ART

Interstitial lung diseases (ILDs) are a group of lung diseases that affect the interstitium, characterized by tissue around alveoli becoming scarred and/or thickened, and so physically inhibiting the respiratory process.

ILDs are distinct from obstructive airway diseases (e.g. chronic obstructive airway disease (COPD) and asthma), which are typically characterized by narrowing (obstruction) of bronchi and/or bronchioles. ILDs may be caused by injury to the lungs, which triggers an abnormal healing response but, in some cases, these diseases have no known cause. ILDs may be triggered by chemicals (silicosis, asbestosis, certain drugs), infection (e.g. pneumonia) or other diseases (e.g. rheumatoid arthritis, systemic sclerosis, myositis, hypersensitivity pneumonitis or systemic lupus erythematosus (lupus)).

The most common ILDs are idiopathic pulmonary fibrosis (IPF), progressive fibrosing ILD (also termed non-IPF progressive fibrotic ILD) and sarcoidosis, both of which are characterized by fibrosis, chronic inflammation and reduced lung function.

IPF in particular is a chronic lung disease characterized by a progressive and irreversible decline in lung function caused by scarring of the lungs. Symptoms typically include cough and shortness of breath.

There are presently no curative treatment options for IPF except, in rare cases, lung transplantation. The disease thus typically presents as a chronic, irreversible, progressive deterioration in lung function and then, in most cases, death within 2-5 years (median survival 2.5 to 3.5 years). While the overall prognosis is poor in IPF, it is difficult to predict the rate of progression in individual patients. Risk factors for IPF include age, male gender, genetic predisposition and history of cigarette smoking.

The annual incidence of IPF is between 5-16 per 100,000 individuals, with a prevalence of 13-20 cases per 100,000 people, increasing dramatically with age (King et al., *Lancet* (2011) 378, 1949-1961; Noble et al., *J. Clin. Invest.* (2012) 122, 2756-2762). IPF is limited to the lungs and is recalcitrant to therapies that target the immune system which distinguishes it from pulmonary fibrosis (PF) associated with systemic diseases.

Patients with IPF usually seek medical assistance due to chronic and progressive exertional dyspnea and cough. Imaging of the lung classically reveals traction bronchiectasis, thickened interlobar septae and subpleural honeycombing. When all three manifestations are present and there is no evidence of a systemic connective tissue disease or environmental exposure, a diagnosis of IPF is very likely. A definite diagnosis is usually made by high-resolution computed tomography (HRCT) and/or lung biopsy, and requires a multidisciplinary team of expertise including pulmonologists, radiologists and pathologists experienced in ILDs.

IPF demonstrates different phenotypes with different prognosis, defined as mild, moderate and severe. Mild cases follow a stable or slow progressive path with patients sometimes taking several years to seek medical advice. Acute exacerbations of IPF are defined as a rapid worsening of the disease, and patients in this sub-population have very poor outcomes with a high mortality rate in the short term.

The cause of IPF is unknown but it appears to be a disorder likely arising from an interplay between environmental and genetic factors resulting in fibroblast driven unrelenting tissue remodeling rather than normal repair; as well as a pathogenesis primarily driven by fibrosis rather than inflammation. A growing body of evidence suggests that the disease is initiated through alveolar epithelial cell microinjuries and apoptosis, activating neighbouring epithelial cells and attracting stem or progenitor cells that produce the factors responsible for the expansion of the fibroblast and myofibroblast populations in a tumor-like way. The fibroblastic foci secrete exaggerated amounts of extracellular matrix that destroys the lung parenchyma and ultimately leads to loss of lung function.

As a restrictive lung disease, diagnosis and monitoring of IPF may involve use of static spirometry. Here, the only consideration is the volume of air that is exhaled, as opposed to dynamic spirometry, which measures the time taken to exhale a certain volume of air, and is typically used to diagnose obstructive lung diseases, like COPD and asthma.

The most usual and useful static spirometric test to diagnose IPF and/or monitor its progression is the forced vital capacity (FVC) test, in which a subject is urged to breathe in as far as he or she can, and then out as far as he or she can. This test is classified as static because it does not involve an element of time.

On the other hand, a dynamic test, namely the Forced Expired Volume in 1 Second (FEV1) test, in which a subject is urged to breathe in as far as he or she can and then breathe out as fast and far as he or she can, is typically used to diagnose obstructive lung diseases. The volume the subject breathes out in 1 second is the FEV1. FEV1 is commonly expressed as a percentage of FVC (FEV1/FVC×100).

The mean annual rate of decline in lung function (vital capacity) in IPF is within a range of 0.13-0.21 litres. Symptoms often precede diagnosis by 1-2 years and radiographic signs may precede symptoms (Ley et al., *Am. J. Respir. Crit. Care Med.* (2011) 183, 431-440).

Numerous IPF treatment approaches have been tested in pre-clinical models and clinical trials such as anti-inflammatory, immune-modulatory, cytotoxic, general anti-fibrotic, anti-oxidant, anti-coagulant, anti-chemokine, anti-angiogenic drugs as well as RAS-blockers, endothelin antagonists, and sildenafil, all of which have basically been shown to provide limited or no benefits (Rafii R et al., *J. Thorac. Dis.* (2013) 5, 48-73).

In addition to oxygen supplementation, the only medications that are presently used to treat IPF are the anti-fibrotics, pirfenidone or nintedanib, but with only limited success in slowing the progression of the disease.

For example, the review article by Maher and Strek (*Respiratory Research*, 20, 205 (2019)) states that, clinical trials have demonstrated that nintedanib and pirfenidone reduce the decline in lung function in patients with IPF, more specifically reducing the rate of decline (according to FVC measurements) by approximately 50% over the period of a year.

Thus, although nintedanib and pirfenidone are believed to reduce the risk of acute deteriorations in lung function and to improve life expectancy by reducing the rate at which IPF progresses, and also (as reported by Isshiki et al, *Respiratory Medicine*, 187, 106551 (2021)) that they may help protect against acute exacerbation of IPF (AE-IPF; acute respiratory worsening in the absence of other known causes, which has a very poor median survival rate), both of these drugs are only, at best, capable of slowing down the progression of the disease. Furthermore, these drugs commonly cause significant (predominantly gastrointestinal) side-effects, which can sometimes curtail treatment (see e.g. Maher and Strek supra).

As mentioned above, a lung transplant is the only intervention that substantially improves survival in IPF patients. However, complications such as infections and transplant rejection are not uncommon.

Thus, there is a real clinical need for safer and/or more effective treatments if IPF. The development of new treatment strategies for IPF is very important, and a fundamental challenge for the future is to develop appropriate therapeutic approaches that will stop, or even reverse, the progression of the disease.

The Renin-Angiotensin System (RAS) is a key regulator of blood pressure homeostasis. Renin, a protease, cleaves its only known substrate (angiotensinogen) to form angiotensin I (Ang I), which in turn serves as substrate to angiotensin converting enzyme (ACE) to form Ang II. The endogenous hormone Ang II is a linear octapeptide ($Asp^1$-$Arg^2$-$Val^3$-$Tyr^4$-$Ile^5$-$His^6$-$Pro^7$-$Phe^8$)(SEQ ID NO: 1), and is an active component of the renin angiotensin system (RAS).

The angiotensin II type 1 (AT1) receptor is expressed in most organs, and is believed to be responsible for the majority of the pathological effects of Ang II. The safety and efficacy of losartan (an AT1-receptor inhibitor) has recently been investigated in a small uncontrolled open-label pilot trial on IPF (see clinicaltrials.gov website, identifier NCT00879879).

Several studies in adult individuals appear to demonstrate that, in the modulation of the response following Ang II stimulation, activation of the angiotensin II type 1 (AT2) receptor has opposing effects to those mediated by the AT1 receptor.

The AT2 receptor has also been shown to be involved in apoptosis and inhibition of cell proliferation (de Gasparo M et al., *Pharmacol. Rev.*, 2000; 52:415-472).

AT2 receptor agonists have also been shown to be of potential utility in the treatment and/or prophylaxis of disorders of the alimentary tract, such as dyspepsia and irritable bowel syndrome, as well as multiple organ failure (see international patent application WO 99/43339).

The expected pharmacological effects of agonism of the AT2 receptor are described in general in de Gasparo M et al., supra. It is not mentioned that agonism of the AT2 receptor may be used to treat IPF.

International patent application WO 2002/096883 describes the preparation of imidazolyl, triazolyl, and tetrazolyl thiophene sulfonamides and derivatives as AT2 receptor agonists. Of the compounds described in that document (as Example 1) is N-butyloxycarbonyl-3-(4-imidazol-1-yl-methylphenyl)-5-iso-butylthiophene-2-sulfonamide (Compound 21 or, as used hereinafter 'C21'), which was selected for clinical development from a group of about 20 related analogues as a selective AT2 receptor agonist.

Mei et al, Pharm. Res., 161 105223 (2020) reported that C21 prevented cigarette smoke-induced emphysema and improved lung functions in a model of obstructive lung disease (specifically COPD), which, as discussed above, is very different from restrictive lung diseases like IPF.

This notwithstanding, promising findings in preclinical models of IPF (see e.g. Bruce et al, *Br. J. Pharmacol.*, 172, 2219 (2015) and Rathinasabapathy et al, Front. Physiol., 9, 180 (2018)) (see also international patent application WO 2016/139475), led to C21 being clinical developed for use in IPF treatment. More recently, C21 has been put into clinical development as a therapeutic treatment of COVID-19 (see international patent application WO 2021/191582).

In particular, C21 is presently in an ongoing Phase II clinical trial in IPF patients. Although the targeted efficacy endpoint at the outset of this study was a reduction in the deterioration in lung function, as measured by FVC, over time compared to current standard of care in IPF (nintedanib and pirfenidone), as demonstrated hereinafter, we have found, remarkably, that C21 is not only capable of arresting the progression of deterioration in lung function in IPF patients in a clinical setting, but actually at least partially restoring it. This represents an unexpected and extremely important development in the treatment of this debilitating and ultimately fatal disease.

DISCLOSURE OF THE INVENTION

According to a first aspect of the invention, there is provided a method of improving lung function in a patient having IPF which comprises perorally administering a therapeutically-effective amount of C21, or a pharmaceutically-acceptable salt thereof in such a patient, which method of treatment is referred to hereinafter as 'the method of the invention'.

The term 'IPF' will be understood to include not only archetypal IPF, which is the well-known progressive fibrotic ILD, as characterized by accelerated respiratory failure, frequent disease exacerbation and earlier mortality, but also the condition 'progressive fibrosing ILD' (PF-ILD), in which some individuals develop a progressive phenotype similar to IPF (see, for example, Flaherty et al, N. Engl. J. Med., 381, 1718 (2019) and Wells, *Lancet*, 9, 437 (2021)). The PF-ILD phenotype often results from a disease (e.g. connective tissue diseases, such as rheumatoid arthritis, scleroderma, dermatomyositis/polymyositis, associated ILDs (CTD-ILD), fibrotic hypersensitivity pneumonitis (fHP), pneumoconiosis, such as asbestosis, silicosis), sarcoidosis, idiopathic non-specific interstitial pneumonia (NSIP), and unclassifiable ILDs. Regardless of disease trigger, PF-ILD possesses similar risk factors, and progresses through similar mechanisms to archetypal IPF, such as self-sustained dysregulated cell repair, fibroblast proliferation and alveolar dysfunction, and can be targeted in a similar fashion together. For the avoidance of unnecessary duplication, the conditions IPF and PF-ILD are referred to together hereinafter as 'IPF'.

As described hereinafter, we have found that, unlike the existing antifibrotic drug-based treatments of IPF (i.e. nintedanib and pirfenidone, as described above), C21 does not just stop the progression of the disease but actually improves lung function compared to 'baseline' lung function levels (i.e. levels measured before the start of treatment), and is thus capable of treating, or even reversing, the disease, and the symptoms thereof per se, in a therapeutic (e.g. a curative therapeutic) fashion.

In this respect, by 'improving lung function' (in any kind of 'therapeutic' fashion), we mean that C21 is not just capable of having beneficial effects when compared to placebo and/or to otherwise untreated patients, or even compared to the above-mentioned established drug-based IPF therapies, but also that, after several weeks of treatment, it is capable of displaying a clear and statistically significant clinical improvement in, and/or restoration of, lung function, as measured by e.g. lung function tests, such as those described herein, when compared to equivalent baseline lung function test measurements made in the same patients prior to the start of treatment with C21 or salt thereof.

There is thus further provided a method of restoring lung function in a patient having IPF, which comprises perorally administering a therapeutically-effective amount of C21, or a pharmaceutically-acceptable salt thereof in such a patient, which method of treatment is also referred to hereinafter as 'the method of the invention'.

The restoration of lung function in patients may comprise any improvement compared to baseline and, accordingly, there is provided at least partial restoration of lung function, as measured by such lung function tests, as compared to equivalent tests prior to the start of treatment. By 'at least partial restoration' we mean anything from full recovery (i.e. values that are within a normal range for an otherwise healthy (non-IPF) patient, to improvements in lung function of up at least about 1%, e.g. at least about 2%, at least about 3% or at least about 4%, such as at least about 5%, e.g. at least about 6%, including at least about 8% or at least about 10%, including at least about 12% or at least about 13%, including at least about 15%, for example at least about 17.5% or at least about 20%, including at least about 22.5%, e.g. at least about 25%, at least about 30%, at least about 35%, at least about 40%, at least about 45%, at least about 50%, at least about 60%, at least about 70% or even at least about 80% or more, compared to lung function as measured by relevant lung function tests prior to (e.g. in conjunction with the first day of treatment and up to about one month such as within about seven to about ten days of) the start of treatment, within a time period of about 12 weeks, such as about 16 weeks, including about 24 weeks or about 36 weeks or even longer, from said start of treatment.

Thus, essentially, C21 and salts thereof are capable of restoring lung function, and therefore a patient's general health and well-being, by providing a curative therapeutic treatment of IPF. Based on the clinical results, we have good reason to believe that C21 may even be capable of providing at least a partial cure for the disease itself.

By providing 'at least a partial cure' for IPF (which may be used interchangeably with a 'curative treatment' or a 'curative therapeutic treatment' of IPF), we mean that lung function may be restored by the method of the invention to a level that is stabilized (i.e. lung function tests, such as FVC, show no decline from baseline levels measured at the start of treatment), or a level that is improved versus such baseline levels, partially or up to levels that are commonly regarded by physicians as 'normal', in which the patient shows less, or even no, significant ongoing symptoms of IPF.

In view of the observed improvements, which were established in the absence of co-therapy with the aforementioned established antifibrotic IPF therapies (i.e. nintedanib and pirfenidone), C21 or a salt thereof may be employed as a first-line/stand-alone treatment of IPF, in the absence of such other drugs.

For the avoidance of doubt, the improvement in lung function in patients reported hereinafter may be a consequence of improved respiration (i.e. the efficiency of gaseous exchange at a cellular level), or, possibly more likely in view of the rate of improvement that has been observed, may be a consequence of an improvement in the degree of the ability of the lungs to inflate with air in a physical sense (i.e. improved breathing through increased/restored of lung capacity and/or vital capacity, i.e. the amount of air that may be inhaled/exhaled), or may be due to other factors, or a combination of any of these things.

There is thus further provided a method of improving lung (or vital) capacity in a patient having IPF, which comprises perorally administering a therapeutically-effective amount of C21, or a pharmaceutically-acceptable salt thereof in such a patient, which method of treatment is also referred to hereinafter as 'the method of the invention'.

Thus, the methods of the invention may alternatively be described as the use of C21 or a pharmaceutically-acceptable salt thereof in the therapeutic (and/or curative) treatment of IPF as manifest by one or more of:
  improved breathing;
  improved/restored lung/pulmonary ventilation;
  improved/restored ventilatory lung/pulmonary function; and/or
  increased/restored vital capacity (defined as the greatest volume of air that can be expelled from the lungs after taking the deepest possible breath),
in IPF patients, and/or by the use of C21 or a salt thereof in a method of preventing (or eliminating altogether) AE-IPF as defined above.

The method of the invention may also provide for one of more of the improvements mentioned hereinbefore in the complete and/or substantial absence of significant side effects or other drug safety issues, including adverse drug reactions and/or C21-related adverse events (AEs), particularly serious AEs (SAEs).

AEs, adverse drug reactions (ADRs) and SAEs are defined by The International Council for Harmonisation of Technical Requirements for Pharmaceuticals for Human Use (ICH, at Guideline E2A (ICH 1994)).

The term 'AE' includes any untoward medical occurrence in a subject that has been administered an investigation medicinal product (IMP, in this case C21 or salt thereof) and which may or may not have a causal relationship with this IMP. An AE can therefore be any unfavourable and/or unintended sign (e.g. a significant abnormal laboratory finding, symptom), or a disease temporally associated with the use of the IMP, whether or not considered related to the IMP.

An ADR is any noxious and unintended response to an IMP related to any dose of the IMP.

An SAE is any untoward medical occurrence that, at any dose:
  results in death;
  is life-threatening (i.e. an event in which the subject was at risk of death at the time of the event, not an event that hypothetically might have caused death, had it been more severe);
  requires in-patient hospitalisation or prolongation of existing hospitalisation;
  results in persistent or significant disability or incapacity;
  is a congenial anomaly or birth defect; and/or
  is judged medically important (i.e. an event that may not be immediately life-threatening or result in death or hospitalisation, but which may jeopardize the subject or may require intervention to prevent one of the other outcomes listed above).

In this respect, C21 and salts thereof are capable of treating IPF in accordance with the method of the invention in a manner in which, in the consideration of the patient and/or in the medical opinion of his/her physician, any AE, SAE, or other side effects, that may result from using it to treat that patient are outweighed by the positive effects that result from the treatment of the disease per se.

In the method of the invention, C21 and salts thereof may be administered in the form of any formulation that is suitable for peroral administration and delivery, as a complete dosage form, to the gastrointestinal tract. This means that a final dosage form comprising C21-containing formulations should be suitable for swallowing as a whole, complete dosage form for subsequent consumption and/or ingestion within the gastrointestinal tract, and, in use, is swallowed and then consumed and/or ingested within that tract.

Thus, C21 and salts thereof may be provided in the form of powders, simple mixtures, granules, pellets, beads, solutions and/or suspensions. Final dosage forms include pills, tablets, capsules, films, solutions or suspensions (e.g. syrups), powders, cakes and the like.

C21 and salts thereof may thus be presented in the form of a simple mixture with a carrier system, that is any pharmaceutically acceptable inert material that is capable of increasing the mass of a composition, or a component of a composition, in order to provide an appropriately handleable dosage form.

Suitable carriers thus include pharmaceutically acceptable inorganic salts, e.g. sodium chloride, calcium phosphate, dicalcium phosphate hydrate, dicalcium phosphate dehydrate, tricalcium phosphate, calcium carbonate, and barium sulfate; polymers, e.g. (optionally silicified) microcrystalline cellulose, cellulose and crosslinked polyvinylpyrrolidone; starches; sugars and sugar alcohols, e.g. lactose, mannitol, xylitol, isomalt, dextrose; or mixtures of any of the foregoing.

Carrier materials are preferably employed in an amount of between about 5% and about 90% by weight based upon the total weight of the composition comprising C21 or salt thereof. A preferred range is from about 10% to about 80% by weight.

Preferred carrier materials include lactose, xylitol, isomalt, microcrystalline cellulose and, more preferably, mannitol. Carrier compositions may comprise physical mixtures of any of the aforementioned materials and/or may comprise composites of one or more of these materials.

Mixtures of C21/salt with carrier materials may thereafter be filled directly into capsules. Such mixtures may alternatively be granulated into pellets, granules or beads and thereafter loaded into appropriate capsules. Powders, pellets, granules or beads may alternatively be compressed into tablets.

Granulation may be carried out using well known techniques, including dry granulation, wet granulation, melt granulation, thermoplastic pelletising, spray granulation or extrusion/spheronization.

Powders, granulates, pellets or beads comprising C21 or salt thereof may, in addition to a carrier material, also comprise other, commonly employed pharmaceutical additives and/or excipients that are used in the art (see, for example Rowe et al, *Handbook of Pharmaceutical Excipients*, 8th ed. (2017) and the documents cited therein).

Other pharmaceutically acceptable excipients are known to those skilled in the art, such as binders, disintegrants, glidants, lubricants and the like.

Binders may be defined as materials that are capable of acting as bond formation enhancers, which may facilitate the compression of a powder mass into coherent compacts. Suitable binders include polyvinylpyrrolidone, gelatin, sodium alginate, cellulose derivatives, such as low substituted hydroxypropyl cellulose, hydroxypropyl methylcellulose, cellulose gum, (optionally silicified) microcrystalline cellulose and the like. If present, binder is preferably employed in an amount of between about 2% and about 50% by weight based upon the total weight of the composition comprising C21 or salt thereof. A preferred range is from about 5% to about 30% by weight.

Disintegrants or disintegrating agents may be defined as materials that are capable of accelerating to a measurable degree the disintegration/dispersion of a component of a composition comprising C21 or salt thereof, such as a granule or a tablet. This may be achieved, for example, by the material being capable of swelling and/or expanding when placed in contact with aqueous media (particularly bodily fluids including those found in the gastrointestinal tract), thus causing at least part of a dosage form comprising a formulation including C21 or salt thereof to disintegrate when so wetted. Suitable disintegrants include cross-linked polyvinylpyrrolidone, cross-linked sodium carboxymethylcellulose (croscarmellose, e.g. sold under the trademark AC-DI-SOL®, FMC Corp., USA), carboxymethyl starch, natural starch, pre-gelatinised starch, corn starch, potato starch, sodium starch glycolate (e.g., sold under the trademark PRIMOJEL®, DMV International BV, Netherlands), low substituted hydroxypropyl cellulose and the like. Disintegrant (which may comprise one or more of the materials mentioned above) is preferably employed in an amount of between about 1% (e.g. about 5%) and about 40% by weight based upon the total weight of the composition comprising C21 or salt thereof. A preferred range is from about 5% (e.g. about 10%) to about 30% by weight. Preferred disintegrants that are employed include cross-linked polyvinylpyrrolidone, cross-linked sodium carboxymethylcellulose, sodium starch glycolate and, particularly, low substituted hydroxypropyl cellulose.

Glidants are pharmaceutically-acceptable materials that promote powder flow by reducing interparticle friction and/or cohesion (but does not necessarily have an ability to reduce and/or prevent adhesion to external materials, such as capsule filling machines or hoppers). Suitable pharmaceutically-acceptable glidant materials thus include talc, magnesium carbonate or calcium silicate although it is preferred that the glidant is a hydrophilic glidant, such as one or more of the various forms of silica, including fumed/pyrogenic silica or, more particularly, silica gels, silica aerogels and/or colloidal silica.

Lubricants are typically employed when the final dosage form to be swallowed is in the form of a tablet and prevent granules or powders from adhering to punch die/faces and promote smooth ejection from the die after compaction. Suitable lubricants include stearic acid, sodium stearyl fumarate, anhydrous colloidal silica, talc or, preferably, magnesium stearate). When a lubricant is employed it should be used in very small amounts (e.g. up to about 3%, and preferably up to 2%, by weight based upon the total weight of the composition comprising C21 or salt thereof).

Other excipients that may be employed in oral dosage forms include surfactants, wetting agents, flavourings (e.g. lemon, menthol or peppermint powder), sweeteners (e.g.

neohesperidin, sucralose or acesulfame potassium), dyestuffs, antioxidants (which may be naturally occurring or otherwise (e.g. butylated hydroxytoluene (BHT), vitamin C, vitamin E, β-carotene, uric acid, uniquion, superoxide dismutase (SOD), glutathione peroxidase or peroxidase catalase)), preservatives and buffering agents.

These, and the other pharmaceutically-acceptable excipients mentioned herein, may be commercially-available or otherwise are described in the literature, for example, including, for all of these types of excipient, those described in for example, Rowe et al., supra and Remington *The Science and Practice of Pharmacy,* 21st ed., Lippincott Williams and Wilkins, Philadelphia (2006) and the documents referred to therein, the relevant disclosures in all of which documents are hereby incorporated by reference. Otherwise, the preparation of suitable peroral formulations may be achieved non-inventively by the skilled person using routine techniques.

Granules, pellets or beads may be further processed following formation. For example, dry granulates may be broken, ground or milled using a suitable milling technique to produce particulate material of a smaller size, which may also be sieved to separate the desired size fraction. Wet granulates may be screened to break up agglomerates of granules and remove fine material. In either case, the unused undersized (fine), and oversized, material may be reworked to avoid waste.

However, the powder mixture, granulate, tablet or capsule is made, the preparation of the composition should ensure that C21 or pharmaceutically-acceptable salt thereof is homogeneously distributed throughout the carrier material (and/or other excipients that is/are employed).

For simple mixtures, this includes mixing for a time period that provides for a homogeneously-distributed active ingredient, for example as described hereinafter. This is likely to vary according to the equipment used.

The terms 'homogeneous' and 'distributed homogeneously' in the context of the invention mean that there is a substantially uniform content of C21 or salt thereof throughout the carrier material (and/or other excipients that is/are employed). In other words, if multiple (e.g. at least, 2, more preferably about 6, such as about 10 up to about 30 or more if needed) samples are taken from a mixture comprising active ingredient and carrier blend, the measured content of active ingredient that is present as between such samples gives rise to a standard deviation from the mean amount (i.e. the coefficient of variation and/or relative standard deviation) of less than about 8%, such as less than about 6%, for example less than about 5%, particularly less than about 2%.

Preferred mixing equipment include standard mixing equipment, such as tumbler, shaker mixing (e.g. Turbula), convective, hopper, and fluidization blenders. Preferred blenders include V-blenders.

Tablets may be formed by a process of compression/compaction. Direct compression/compaction may be achieved using techniques such as those described in, for example, *Pharmaceutical Dosage Forms: Tablets.* Volume 1, 3rd Edition, Augsburger et al (eds.), CRC Press (2008) and the documents cited therein. Suitable compacting equipment includes standard tabletting machines, such as the Kilian SP300 or the Korsch EK0.

It is preferred that the composition comprising C21 or salt thereof is contained within a capsule that is suitable for such peroral administration.

Appropriate pharmaceutically-acceptable capsules include soft-shell or hard-shell capsules, which can be made from gelatin, cellulose polymers, e.g. hydroxypropyl methylcellulose (HPMC or hypromellose), hypromellose acetate succinate (HPMCAS), starch polymers, pullulan or other suitable materials, for example by way of standard capsule filling processes.

When dosage forms comprises a solid formulation comprising a mixture of C21 or salt thereof along with carrier materials (e.g. in the form of a powder, granules and the like), in accordance with a preferred aspect of the invention, capsules are preferably hard-shell, two-piece capsules, for example capsules that are made from gelatin or, more preferably, HPMC and are supplied as closed halves that may be separated and filled with particulate matter, followed by re-assembly. Such capsules may be of any size (e.g. 00 to 5), but preferred capsule sizes are size 2, size 1 or, more preferably, size 0.

In this, and other, preferred embodiments of the invention, C21 or salt thereof is presented in the form of particles, which may be amorphous or crystalline or a mixture of the two. Preferred particles are of a size that will not lead to segregation, either during formation of the composition to be loaded into capsules during the capsule-loading process or upon storage.

In this respect, C21 or salt thereof may be provided in the form of a plurality of primary (i.e. non-agglomerated) particles typically having a weight- and/or a volume-based mean diameter of no more than about 1,000 µm, such as about 500 µm, including about 250 µm, preferably no more than about 100 µm, including no more than about 50 µm, such as about 20 µm, or no more than about 10 µm. Although there is no lower limit on particle sizes that may be employed in accordance with this aspect of the invention, for ease of manufacture, we prefer that primary particles of C21 or salt thereof have weight- and/or volume-based mean diameter of no less than about 1 µm, such as about 2 µm, including about 3 µm.

As used herein, the term 'weight based mean diameter' will be understood by the skilled person to include that the average particle size is characterised and defined from a particle size distribution by weight, i.e. a distribution where the existing fraction (relative amount) in each size class is defined as the weight fraction, as obtained by e.g. sieving (e.g. wet sieving). The term 'volume based mean diameter' is similar in its meaning to weight based mean diameter, but will be understood by the skilled person to include that the average particle size is characterised and defined from a particle size distribution by volume, i.e. a distribution where the existing fraction (relative amount) in each size class is defined as the volume fraction, as measured by e.g. laser diffraction. Particle sizes may also be measured by standard equipment, such as a dry particle size measurement technique, including dry dispersion technologies available from manufacturers such as Sympatec GMbH (Clausthal-Zellerfeld, Germany). Other instruments that are well known in the field may be employed to measure particle size, such as equipment sold by e.g. Malvern Instruments, Ltd. (Worcestershire, UK), Shimadzu (Kyoto, Japan) and (Elzone, Micromeritics (USA; electrical sensing zone method).

By particles having weight- and/or volume-based mean diameters within the above limits, we include mean diameters of particles when prepared and prior to mixing with the relevant excipients according to the invention, and/or prior to being loaded into capsules. It will be appreciated that some aggregation of primary particles to form secondary particles may occur during handling and/or processing of active ingredient. This should nevertheless be minimised.

C21 or salt thereof may also be provided in the form of particles with a relative narrow particle size distribution (PSD), as measured by standard techniques and art-accepted parameters, including mass median diameter ($D_{50}$; the log-normal mass median diameter), the average particle size by mass and/or the diameter at which 50% of the mass in the cumulative PSD are contained) and/or geometric standard deviation (GSD or a as measured by the formula $D_{84.13}/D_{50}$ or $D_{50}/D_{15.78}$, where $D_{84.13}$ and $D_{15.78}$ are respectively the diameters at which 84.13% and 15.78% of the mass are contained, and $D_{50}$ is as hereinbefore defined). Such parameters may be measured and calculated in-process using any appropriate sampling method and particle size measurement technique as described hereinbefore.

It is preferred in this respect that C21 or salt thereof has a PSD with a GSD that is less than about 4, such as less than about 3.

Primary particles of C21 or salt thereof may be prepared by an appropriate technique, such as precipitation, cutting (e.g. by way of dissolution in a supercritical fluid under pressure, followed by rapid expansion), spray drying, or may, if appropriate, be micronized by techniques that are well known to those skilled in the art, such as grinding, dry milling, jet milling, wet milling and/or crushing.

Particles may also be sieved to separate into a desired size fraction, and/or screened to break up agglomerates and/or remove fine material. In either case, unused undersized (fine), and oversized, material may be reworked to avoid waste.

Alternatively, particles may be separated into appropriate particle sizes using cyclonic separation, by way of an air classifier, sedimentation, force-field fractionation and/or elutriation.

Although C21 or salt thereof may be selected and/or provided with the aforementioned weight- or volume-based mean diameters, particle sizes, PSDs and/or GSDs using one or more of the above techniques, one of the primary benefits of formulating the compositions that are to be loaded into capsules to form dosage forms for administration, is that C21 or salt thereof does not require the particle processing techniques that are described above prior to blending with relevant excipients.

In this respect, and as mentioned hereinbefore, we have found that C21 and salts thereof are extremely difficult materials to work with. Part of the issue is the extreme sensitivity of C21 and salts thereof to the combined presence of light and water.

Furthermore, in particular and as described hereinafter, compatibility studies have revealed that certain standard excipients, when co-mixed with C21 and salts thereof give rise to significant chemical instability of the active ingredient. Furthermore, C21 and salts thereof are formed as needle-like crystals that are sticky and have a tendency to agglomerate. This means that dry mixing with certain standard pharmaceutically-acceptable ingredients is very difficult, and it is not straightforward to produce blends with pharmaceutically-acceptable content uniformities of active ingredient, and/or dose uniformities the same within capsules.

Further, it has been found that micronizing primary particles of active ingredient has also not provided a solution to these problems, as the skilled person might have expected to be the case, and also gives rise to additional problems connected with localised heating and static electricity.

However, we have found that by blending C21 or pharmaceutically-acceptable salt thereof with a pre-mixed blend of carrier particles having a weight- and/or a volume-based mean diameter, and/or a structural (particle) density, that is/are similar to the weight- and/or volume-based mean diameter, and/or the structural (particle) density, of the solid particles of C21, or a pharmaceutically-acceptable salt thereof, and a glidant, it is possible to avoid the aforementioned problems and to provide a composition for loading into capsules in which C21 or salt thereof is not only homogeneously and evenly distributed, ensuring dose homogeneity of active ingredient between capsules following such loading, but is also physically and chemically stable, during and after manufacture, under normal storage conditions, and during use.

Thus, in this aspect, methods of the invention comprise the administration of dosage forms comprising excipients that are admixed with particles of C21 or pharmaceutically-acceptable salt thereof comprise a blend of at least one type of carrier particles with a weight- and/or a volume-based mean diameter, and/or a structural (particle) density, that is/are similar to the weight- and/or volume-based mean diameter, and/or the structural (particle) density, respectively, of the solid particles of C21, or a pharmaceutically-acceptable salt thereof, and a glidant.

The terms 'homogeneous' and 'distributed homogeneously' in the context of this aspect are as hereinbefore defined.

In this preferred aspect of the invention, suitable carrier particle materials may comprise pharmaceutically-acceptable substances that are soluble in water, including carbohydrates, such as sugar alcohols, such as sorbitol, xylitol and, particularly, mannitol. Again, carrier particles may comprise physical mixtures of any of these materials and/or may comprise composites of one or more of these materials.

The carrier particles have a similar particle size distribution and/or structural (particle) density as the active ingredient particles that are employed in compositions to be loaded into capsules to make such dosage forms.

By 'similar particle size distribution and/or structural (particle) density' we mean that the weight- and/or volume-based mean diameter, and/or particle density, of the carrier particles is within about ±75%, such as about ±50%, including about ±40%, e.g. about ±30%, or about ±20% including about ±10% of the relevant dimensions of the C21 or salt thereof that is employed.

In this respect, preferred carrier particle sizes include weight- and/or a volume-based mean diameter that are less than about 100 μm, including less than about 80 μm, such as less than about 70 μm, for example between about 20 μm and about 60 μm (e.g. about 25 μm or, more preferably, about 50 μm).

We have found that, by employing carrier particles with sizes that are similar to those of the active ingredient and/or within the above ranges, blend segregation is avoided.

Thus, to make compositions to be loaded into capsules to make dosage forms in accordance with this aspect of the invention, prior to mixing with active ingredient, carrier particles of the requisite size are pre-blended with a suitable glidant material, preferably a proprietary silica sold under the trademark SYLOID® (see grace.com website), a colloidal silica, and/or fumed/pyrogenic silica. Preferred forms of silica thus include stable aqueous dispersions (sols) of amorphous silica particles with a weight- and/or a volume-based mean diameter that is between about 1 nm and about 100 nm (e.g. up to about 50 nm, such as up to about 20 nm, such as between about 10 nm and about 15 nm).

It is preferred therefore that the glidant and the carrier particles are mixed together to form an interactive (or an ordered) mixture of carrier particles that are largely coated with smaller particles of a glidant material, which blend is then admixed with active ingredient particles.

We have also found that by adding the aforementioned glidant to the carrier particles to first form an excipient blend, prior to mixing with active ingredient, this improves the flow properties of that excipient blend, and so leads subsequently to better mixing with C21 or pharmaceutically-acceptable salt thereof, further decreasing the likelihood of blend segregation.

In this aspect of the invention, dosage forms may also include other excipients that are well known to those skilled in the art for peroral delivery of active ingredients, such as those mentioned hereinbefore.

However, in view of the extreme sensitivity of C21 and salts thereof to other chemicals, it is preferred that such other excipients are not included in dosage forms according to this aspect of the invention. In this respect, dosage forms may consist essentially of a pharmaceutical composition in the form of a particulate mixture comprising solid particles of C21, or a pharmaceutically-acceptable salt thereof, admixed with a blend of carrier particles with a weight- and/or a volume-based mean diameter, and/or a structural (particle) density, that is/are similar to the weight- and/or volume-based mean diameter, and/or the structural (particle) density, of the solid particles of C21, and a glidant, which composition is contained within a capsule that is suitable for such peroral administration.

All preferred features mentioned herein for other aspects of the invention which relate in any way to this aspect of the invention are equally applicable.

The term 'consisting essentially of' will be understood to mean that the scope of this (and only this) aspect of the invention is limited to the specified essential features mentioned above, along with other features that do not materially affect the basic and novel characteristic(s) of this aspect of the invention.

In this respect, although not an essential feature of this aspect of the invention, it may be preferable to add a lubricant (such as sodium stearyl fumarate or, preferably, magnesium stearate) to the blend prior to filling into capsules, in order to prevent the blend from adhering to equipment (e.g. capsule filling machines and hoppers). This is a preferred feature that does not materially affect the basic and novel characteristics of this aspect of the invention.

Compositions to be loaded into a capsule that 'consist essentially of' a particulate mixture comprising solid particles of C21, or pharmaceutically-acceptable salt thereof, admixed with a blend of carrier particles as defined above and a glidant may alternatively mean that the composition comprises at least about 95%, such as at least about 97% by weight of those particular ingredients in total.

In this aspect of the invention, it is also preferred that the dry mix blend is passed through a sieve at points during the mixing process in order to break up agglomerates that are formed during the blending process, for example as described hereinafter. A suitable sieve is one that has a pore size that is of a size that is as small (or thereabouts) as the particle size of the largest component of the blend. Thus, suitable sieve sizes are about 50 μm, e.g. 75 μm, including 100 μm, such as 150 μm, 200 μm or 250 μm (e.g. about 300 μm) up to about 1,000 μm, such as about 400 μm (e.g. about 500 μm) up to about 900 μm (e.g. about 800 μm).

Dosage forms may also be presented in the form of a heterogeneous mixture comprising solid particles of C21, or a pharmaceutically-acceptable salt thereof, suspended in a pharmaceutically-acceptable, hydrophobic, lipid-based carrier in which C21 or salt thereof is essentially insoluble, which composition is loaded into a capsule that is suitable for such peroral administration.

Lipid-based carrier systems within which solid particles of C21 or salt thereof are suspended may be in the form of solids at room temperature (fats) or, more preferably, may in the form of liquids at room temperature (oils). Particles of C21 or salt thereof may nevertheless be suspended in either form of lipid carrier.

In accordance with this aspect, we prefer that the capsules are soft-shell, single-piece capsules, for example soft gelatin capsules, in which a single-piece gelatin capsule is filled with a lipid-based suspension of C21 or salt thereof, and thereafter sealed hermetically as a single piece, for example with a drop of gelatin solution. Gelatin may be obtained from any source (e.g. porcine and bovine sources), but it should be noted that there are vegan alternatives to soft gelatin capsules.

Soft gelatin capsule shells may comprise one or more plasticisers, such as xylitol, sorbitol, polyglycerol, non-crystallizing solutions of sorbitol, glucose, fructose and glucose syrups, more preferably glycerin/glycerol, sorbitol and/or proprietary plasiticizers, such as Anidrisorbs (proprietary mixtures of sorbitol, sorbitans, maltitol and mannitol, Roquette Freres, including Anidrisorb 85/70 (a liquid sorbitol-mannitol-hydrolyzed starch plasticizer)). Soft gelatin capsule shells optionally comprise one or more flavouring agents, colouring agents and/or opacifiers (such as titanium dioxide).

Such capsules may be of any shape (e.g. oblong, round, oval, tubular, etc.) and of any size (e.g. 3 to 24 oblong, 1 to 20 round, 2 to 20 oval, 5 to 120 tube, etc.). Preferred capsule sizes will hold a volume of between about 0.3 and about 1.0 mL.

It is essential in this particular aspect of the invention that C21 or pharmaceutically-acceptable salt thereof is essentially insoluble within the lipid-based carrier under normal storage conditions. By 'essentially insoluble' we include that C21 or salt thereof has a solubility within that carrier that is no more than about 0.015 mg of C21 or salt thereof per gram of carrier.

In this way, because of the carrier's dual properties of hydrophobicity and lack of propensity to dissolve C21 or salt thereof, the active ingredient is not exposed to amounts of water that may catalyze its degradation as described hereinbefore.

We have found, surprisingly, that there are relatively few lipid-based carrier materials that meet these requirements and are therefore able to stabilize C21 or salts thereof at ambient temperatures in such dosage forms.

Hydrophobic lipid-based carrier materials in which C21 or salt thereof must be insoluble as hereinbefore defined may comprise a non-polar oil or fat that is essentially non-miscible with water. It is preferred that the lipid-based carrier is mainly comprised of triacylglycerols (also known as 'triglycerides'), which are esters formed by reaction of all three hydroxyl groups of a glycerol moiety with fatty (carboxylic) acids.

Lipids may thus contain saturated or unsaturated chain fatty acids, which chain can range from 1 carbon atom up to 30 carbon atoms, including up to 26 carbon atoms, such as up to 22 carbon atoms, including 8, 10, 12, 14, 16, 18 or 20 carbon atoms, etc.

Saturated fatty acids that may be mentioned include acetic acid (2), propionic acid (3), butyric acid (4), valeric acid (5), caproic acid (6), enanthic acid (7), caprylic acid (8), pelargonic acid (9), capric acid (10), undecylic acid (11), lauric acid (12), tridecylic acid (13), myristic acid (14), pentadecylic acid (15), palmitic acid (16), margaric acid (17), stearic acid (18), nonadecylic acid (19), arachidic acid (20), heneicosylic acid (21), behenic acid (22), tricosylic acid (23), lignoceric acid (24), pentacosylic acid (25), cerotic acid (26), carboceric acid (27), montanic acid (28), nonacosylic acid (29) and melissic acid (30), wherein the numbers in brackets are the number of carbon atoms in the fatty acid molecule.

Unsaturated fatty acids that may be mentioned include crotonic acid (4:1), as well as ω-3 unsaturated fatty acids, such as octanoic acid (8:1), decanoic acid (10:1), decadienoic acid (10:2), lauroleic acid (12:1), laurolinoleic acid (12:2), myristovaccenic acid (14:1), myristolinoleic acid (14:2), myristolinolenic acid (14:3), palmitolinolenic acid (16:3), hexadecatrienoic acid (16:3), palmitidonic acid (16:4), α-linolenic acid (18:3), stearidonic acid (18:4), 11,14,17-eicosatrienoic acid (20:3), eicosatetraenoic acid (20:4), eicosapentaenoic acid (20:5), heneicosapentaenoic acid (21:5), clupanodonic acid (22:5), docosahexaenoic acid (22:6), 9,12,15,18,21-tetracosapentaenoic acid (24:5), herring acid (24:6) and 6,9,12,15,18,21-tetracosahexaenoic acid (24:6); ω-5 unsaturated fatty acids, such as myristoleic acid (14:1), palmitovaccenic acid (16:1), α-eleostearic acid (18:3), β-eleostearic acid (trans-18:3), punicic acid (18:3), 7,10,13-octadecatrienoic acid (18:3), 9,12,15-eicosatrienoic acid (20:3) and β-eicosatetraenoic acid (20:4); ω-6 unsaturated fatty acids, such as tetradecenoic acid (14:1), 12-octadecenoic acid (18:1), linoleic acid (18:2), linolelaidic acid (trans-18:2), γ-linolenic acid (18:3), calendic acid (18:3), pinolenic acid (18:3), 11,14-eicosadienoic acid (20:2); dihomo-linoleic acid (20:2), dihomo-γ-linolenic acid (20:3), arachidonic acid (20:4), docosadienoic acid (22:2), adrenic acid (22:4), osbond acid (22:5), tetracosatetraenoic acid (24:4) and tetracosapentaenoic acid (24:5); ω-7 unsaturated fatty acids, such as 5-dodecenoic acid (12:1), 7-tetradecenoic acid (14:1), palmitoleic acid (16:1), vaccenic acid (18:1), rumenic acid (18:2), paullinic acid (20:1), 7,10,13-eicosatrienoic acid (20:3), 15-docosenoic acid (22:1) and 17-tetracosenoic acid (24:1); ω-9 unsaturated fatty acids, such as hypogeic acid (16:1), oleic acid (18:1), elaidic acid (trans-18:1), gondoic acid (20:1), 8,11-eicosadienoic acid (20:2), erucic acid (22:1), nervonic acid (24:1), mead acid (20:3) and ximenic acid (26:1); ω-10 unsaturated fatty acids, such as sapienic acid (16:1); ω-11 unsaturated fatty acids, such as gadoleic acid (20:1); and ω-12 unsaturated fatty acids, such as 4-hexadecenoic acid (16:1), petroselinic acid (18:1) and eicosenoic acid (20:1), wherein the numbers in brackets are, respectively, the number of carbon atoms, and number of unsaturated (i.e. double) bonds, in the fatty acid molecule.

Fatty acids that may be mentioned include caproic acid, caprylic acid, capric acid, lauric acid, myristic acid, palmitic acid, stearic acid, oleic acid, ricinoleic acid, linoleic acid, linolenic acid, eicosenoic acid, behenic acid and erucic acid.

Triglycerides may be naturally-occurring oils or fats, may be semi-synthetic or may be synthetic.

Naturally-occurring oils or fats may be obtained from an animal or, more preferably, vegetable sources, such as seeds, kernels, or fruits.

Naturally-occurring vegetable oils comprise, principally, triglycerides, which are mixtures of glycerides with differing fatty acid chain lengths.

Naturally-occurring pharmaceutically-acceptable oils that fall into this category include sunflower oil, soybean oil, corn oil, grape seed oil, rapeseed oil, sesame oil, almond oil, apricot kernel oil, cotton seed oil, palm kernel oil, castor oil, olive oil, palm oil and coconut oil (for respective compositions see, for example, *Occurrence and Characteristics of Oils and Fats* at pages 47-224 in Padley, Gunstone and Harwood (Eds.), *The Lipid Handbook*, Chapman & Hall, London, 1994).

When employed in such dosage forms, naturally-occurring oils should be pharmaceutical grade and should therefore preferably be refined after extraction from their natural source(s). This may be done using techniques that are well known to those skilled in the art.

Preferred oils include one or more of sesame oil, corn oil, palm kernel oil, coconut oil or soya oil.

Semi-synthetic and synthetic lipid-based carrier systems may be made using techniques that are well known to those skilled in the art, for example separation, interesterification, fat splitting and transesterification (glycerolysis).

Semi-synthetic and synthetic lipid based carrier systems thus include those that are typically in the form of oils, including short chain ($C_1$ to $C_5$) triglycerides (such as triacetin) and medium chain ($C_6$ to $C_{12}$) triglycerides (the primary component of the naturally-occurring oils palm kernel and coconut oils, such as capric triglycerides, more specifically those sold under the trademark MIGLYOL® 812N); and those that are often in the form of semi-solid fats, including long chain ($C_{14}$ to $C_{22}$) triglycerides (such as those sold under the trademark GELUCIRE®43/0110).

Whatever form of hydrophobic lipid-based carrier system is employed, it is preferred that the principal component of the carrier system comprises at least about 85% triacylglycerols, more preferably at least about 90% triacylglycerols, and especially at least about 95% triacylglycerols.

Mixtures of any of the above-mentioned naturally-occurring, semi-synthetic and/or synthetic lipid-based carrier materials may be employed.

In this aspect of the invention, C21 or salt thereof is presented in the form of particles, which may be amorphous or crystalline or a mixture of the two. Preferred particles are of a size that will not lead to sedimentation, either during formation of the suspension, the capsule loading process or upon storage.

In this respect, C21 or salt thereof may be provided for suspension in the lipid-based carrier in the form of a plurality of primary (i.e. non-agglomerated) particles typically having a weight- and/or a volume-based mean diameter (as hereinbefore defined) with the same ranges and values as those described hereinbefore for the preferred solid dosage forms that may be employed in methods of the invention.

By particles having weight- and/or volume-based mean diameters within the aforementioned limits, we include that mean diameters of particles when prepared and prior to suspension in the lipid-based carrier, when so suspended and/or prior to being loaded into capsules as described herein. Primary particles of C21/salt thereof may thus be prepared as described hereinbefore.

It is important to ensure that, prior to loading of the suspension of this aspect of the invention into capsules, it comprises C21 or salt thereof homogenously and evenly distributed throughout the suspension, to ensure dose homogeneity of active ingredient following such loading into capsules. Accordingly, C21 and salts thereof are preferably provided in the form of particles with a relative PSD as hereinbefore defined.

Although C21 or salt thereof may be selected and/or provided with such a PSD and/or GSD using one or more of the above techniques to provide a stable suspension with an even distribution of C21/salt particles within that suspension, it is important to ensure thorough mixing of C21/salt with the lipid-based carrier system to ensure that an even distribution of active ingredient particles within the carrier is provided prior to loading. This is particularly so in the case of a bulk suspension that is employed as part of a capsule-loading process, where it is important to ensure that the mixture is homogeneous, not only at the outset, but also that this homogeneity is retained during the loading process to ensure dose homogeneity within a production batch.

The terms 'homogeneous' and 'distributed homogeneously' mean that there is a substantially uniform content of C21 or salt thereof throughout the lipid-based carrier material, and are defined hereinbefore.

If the lipid-based carrier system is in the form of a fat (i.e. a solid or a semi-solid at or around normal manufacturing temperatures and/or product storage temperatures), the skilled person will appreciate that the fat will need to be melted by raising the temperature prior to mixing.

Further, in order to ensure that such a suspension provides for a stable, homogeneous even distribution of active ingredient within the carrier, if necessary, the lipid-based carrier system (and particularly those that are in the form of an liquid oil at or around normal manufacturing temperatures and/or product storage temperatures) may further comprise a thickening agent to avoid particle aggregation and/or sedimentation, such as microcrystalline cellulose and carboxymethylcellulose sodium, as well as blends of mono, di- and triglycerides with PEG esters of unsaturated fats, such as Gelucire 43/01, hydrogenated vegetable oil, beeswax, paraffin wax, etc.

By presenting C21, or salt thereof, in the form of a suspension of particles in accordance with this aspect of the invention, we have found that the aforementioned dosage forms are not only capable of delivering a consistent and/or uniform dose of active ingredient, but also that it is possible to ensure that the active ingredient remains in a form in which it is both physically and chemically stable during and/or after manufacture, under normal storage conditions, and/or during use.

As employed herein, C21, or pharmaceutically-acceptable salt thereof, can be made and stored in the form of composition that may be used directly in the manufacture of dosage forms to be employed in methods of the invention, and furthermore, once made, such dosage forms may be stored under normal storage conditions, with an insignificant degree of changes in physico-chemical properties of the dosage form, composition mixture contained therein and/or, most importantly, active ingredient, over time.

An 'insignificant degree of changes in physico-chemical properties' thus includes that compositions comprising C21/salt in an appropriate carrier as hereinbefore described, before and/or after having been mixed with appropriate excipients, loaded into capsules, compressed into tablets or otherwise, may possess both physical stability and chemical stability.

By 'chemical stability', we include that compositions comprising C21/salt in an appropriate carrier, and dosage forms including them, may be stored (with or without appropriate pharmaceutical packaging), under normal storage conditions, with an insignificant degree of chemical degradation or decomposition of such dosage forms and/or compositions contained therein, and particularly the active ingredient.

By 'physical stability', we include that compositions comprising C21/salt in an appropriate carrier, and dosage forms including them, may be stored (with or without appropriate pharmaceutical packaging), under normal storage conditions, with an insignificant degree of physical transformation, such as aggregation, separation or segregation, or sedimentation, as described above, or changes in the nature and/or integrity of such dosage forms and/or compositions contained therein, and particularly the active ingredient, including dissolution, solvatisation, solid state phase transition, etc.

Examples of 'normal storage conditions' include temperatures of between minus 80 and plus 50° C. (preferably between 0 and 40° C. and more preferably ambient temperature, such as between 15 and 30° C.), pressures of between 0.1 and 2 bars (preferably atmospheric pressure), relative humidities of between 5 and 95% (preferably 10 to 60%), and/or exposure to 460 lux of UV/visible light, for prolonged periods (i.e. greater than or equal to six months).

Under such conditions, C21, salt thereof, and/or compositions containing them, may be found to be less than about 15%, more preferably less than about 10%, and especially less than about 5%, physically and/or chemically transformed. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

It is preferred that pharmaceutical compositions, whether in the form of a dry powder mixture, a lipid-based suspension or otherwise, and/or whether contained within a capsule as described above or otherwise, are manufactured and/or stored in a manner in which they are kept essentially free of water.

By 'essentially free of water', we include that appropriate precautions are taken to ensure that both particles C21 or salt thereof, and the excipients with which it is mixed, are individually prepared and/or provided in a manner in which they are essentially dry, and are also mixed together to form dry mixture in an environment in which they are kept essentially dry.

By 'essentially dry' or 'essentially free of water', we include that the composition comprising C21/salt and relevant excipients comprises, as a whole, no more that about 5%, including no more than about 2%, such as no more than about 1%, including no more than about 0.5%, such as about 0.1% water or less.

Further processing of compositions comprising C21 or salt thereof and relevant excipients into dosage forms as described hereinbefore may also preferably take place in a manner in which it is kept in such an essentially water-free state.

In this respect, although pharmaceutically-acceptable capsule materials may contain residual amount of water, ingress of water into the composition (whether in the form of a solid (e.g. a powder mixture) or a liquid (e.g. a lipid suspension)) from the capsule material should be minimised, so protecting the highly sensitive C21 or salt thereof from contact with water and therefore, in the presence of light, degradation.

It is nevertheless preferred (although not necessarily essential) to package dosage forms in a manner that keeps the dosage form itself dry and protected from light. This may include hermetically-sealed packaging, use of deliquescent materials, etc.

In a further aspect of the invention, C21 and salts thereof may be presented in any pharmaceutical dosage form, including those described hereinbefore that is capable of being coated, surrounded and/or encapsulated by an enteric substance to make a final dosage that is suitable for peroral administration to the gastrointestinal tract.

Enteric substances may be used to coat a variety of dosage forms, including the numerous formulation/dosing principles described hereinbefore a non-limiting sense. For example, compositions may be loaded into capsules, or compressed into tablets, that are suitable for peroral administration and may be coated with an enteric substance.

In this respect, when C21 or salt thereof is provided in a multiparticulate form, such as a powder, as granules, pellets and/or beads, particles may be coated, either individually or collectively, with an enteric substance. This may be done in a variety of ways, for example by filling such multiparticulates into capsules, along with any relevant excipients, such as solid carrier substances (e.g. carrier particles) or liquid (e.g. oil-based) carrier materials as described above, prior to application of an enteric substance on the exterior of the capsule. Alternatively, particles, including granules or pellets, comprising C21 or salt thereof may be individually coated with an enteric substance prior to loading into an appropriate capsule, optionally along with other excipient materials.

Similarly, C21/salt and excipients as described above may be compressed into tablets prior to coating with an enteric substance.

As defined herein, an 'enteric' substance may be employed to coat, surround and/or encapsulate a composition comprising C21 or a pharmaceutically-acceptable salt thereof, in order to substantially prevent the active ingredient from being released from that composition within the stomach, and/or coming into contact with gastric juices, and/or until that component reaches the small intestine. By 'substantially preventing', we include that no more than about 20%, such as about 15%, for example about 10%, or more particularly no more than about 5%, of the active ingredient is released within the acidic environment of the stomach.

Typical enteric coating materials include the following: cellulose acetate, cellulose acetate succinate, cellulose acetate phthalate, cellulose acetate tetrahydrophthalate, polyvinyl acetate phthalate, hydroxyethyl ethyl cellulose phthalate, methacrylic acid copolymers, polymethacrylic acid/acrylic acid copolymers, styrol maleic acid copolymers, hydroxypropyl methyl cellulose phthalate, acrylic resins, cellulose acetate trimellitate, hydroxypropyl methylcellulose trimellitate, shellac, hydroxyethyl ethyl cellulose phthalate, carboxymethylcellulose and hydroxypropyl methyl cellulose acetate succinate. Preferred enteric substances include polyvinyl acetate phthalate and, particularly, methacrylic acid copolymers.

Pharmaceutically-acceptable salts of C21 include acid addition salts. Such salts may be formed by conventional means, for example by reaction of C21 in the form of the free acid (hereinafter 'free C21') with one or more equivalents of an appropriate acid, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of an active ingredient in the form of a salt with another counter-ion, for example using a suitable ion exchange resin. Preferred salts of C21 include HCl salts, alkaline earth salts, such as magnesium and calcium salts, and alkali metal salts, such as potassium or, preferably, sodium salts.

The amount of C21 or salt thereof in a dosage form for use in a method of the invention will depend, and/or may be selected depending, upon the severity of the relevant condition (i.e. IPF), or the expectation of such severity, as well as on the patient, to be treated, but may be determined by the skilled person. The mode of administration may also be determined by the timing and frequency of administration, as well as the severity of the condition.

Suitable lower daily doses of C21 in adult patients (average weight e.g. 70 kg) for use in the method of the invention, calculated as the dose of free C21 in a relevant dosage form, may be about 10 mg, such as about 20 mg, for example about 25 mg, per day. Suitable upper limits of daily dose ranges of C21 calculated as the dose of free C21 in a relevant dosage form, may be about up to about 900 mg, such as 600 mg, including about 400 mg. In particular, daily doses may be about 300 mg, such as about 250 mg, including about 200 mg, such as about 175 mg or about 150 mg, including about 100 mg, and including about 75 mg or about 50 mg.

All of the above doses are calculated as free C21. Doses may be split into multiple individual doses per day. Doses may be given between once and six, such as four times daily, preferably three times daily and more preferably twice daily.

The above-mentioned doses, particularly those at the higher levels mentioned above, may also be considered to part of an 'induction' phase of the treatment of IPF. Furthermore, after the medical practitioner or a skilled person has determined that induction phase has been successful, for example by it resulting in a significant improvement/restoration of lung function or capacity as hereinbefore defined, C21 or salt thereof may thereafter be administered at an appropriate dose, as part of a 'maintenance' treatment of that disorder. Appropriate maintenance doses on a daily basis may be in the lower ranges mentioned above, such as up to about 150 mg, including up to about 100 mg, up to about 75 mg, up to about 50 mg, up to about 40 mg, up to about 30 mg or up to about 25 mg, or even lower than that. Alternatively, appropriate induction or maintenance doses may be administered a less frequent basis, for example by way of an extended release peroral dosage form, which gives rise to equivalent plasma concentration profiles to the once daily doses mentioned above.

In any event, the medical practitioner, or other skilled person, will be able to determine routinely the actual dosage, which will be most suitable for an individual patient, depending on the severity of the condition and route of administration. The above-mentioned dosages are exemplary of the average case; there can, of course, be individual instances where higher or lower dosage ranges are merited, and such are within the scope of this invention.

The dose administered to a patient, in the context of the present invention should be sufficient to affect an appropriate response in the patient over a reasonable timeframe (as described hereinbefore). One skilled in the art will recognize that the selection of the exact dose and composition and the most appropriate delivery regimen will also be influenced by inter alia the pharmacological properties of the formulation, the nature, stage and/or severity of the condition being treated, the physical condition and mental acuity of the recipient, including the age, condition, body weight, sex and response of the patient to be treated, and the stage/severity of the disease, and genetic differences between patients.

In relation to the nature, stage and severity of IPF, it is to be noted that there are presently no generally accepted or validated staging systems. There is an abundance of data on using information acquired from physiological, radiological and pathological parameters, in isolation or in combination, to assess disease severity in IPF. Recently, there has been interest in using serum biomarkers and computed tomography-derived quantitative lung fibrosis measures to stage disease severity in IPF (see Robbie et al, Eur. Respir. Rev. 26, 17005 (2017). However, Lopes et al (*Clinics* (Sao Paulo), 66, 1015 (2011) suggested a classification system for IPF based on the 95% confidence interval of the FVC as follows: mild (≥92.7%); moderately mild (76.9-92.6%); moderate (64.3-76.8%); moderately severe (47.1-64.2%); severe (24.3-47.0%); and very severe (<24.3%), which classification. An alternative classification system for IPF based on FVC is as follows: mild (>80%); moderate (50-80%); and severe (<50%).

Methods of the invention may be used to treat IPF, as well as conditions that may trigger IPF, such as systemic sclerosis, rheumatoid arthritis, myositis or systemic lupus erythematosus, or are otherwise associated with IPF, such as pulmonary hypertension and/or pulmonary arterial hypertension.

Although the remarkable results described hereinafter might be at least in part due to C21's anti-fibrotic effect (e.g. as characterised by a reduction of fibrosis and/or prevention of further deposition of extra cellular matrix, reversal of these fibrotic phenomena, including lung scarring/wound healing, reduction in proliferation of fibroblasts and myofibroblasts, vascular remodelling, etc.), it is to be noted that corresponding effects are not seen by existing anti-fibrotic IPF therapies (such as nintedanib and pirfenidone). Without being limited by theory therefore, we do not believe that these entirely unexpected results can be explained solely by C21's known anti-fibrotic effect and, accordingly, the precise mechanism behind them is not presently understood.

Although primarily indicated in the therapeutic (including the curative and/or restorative) treatment of lung function in IPF patients, C21 and salts thereof may, at the same time, be useful in palliative and/or diagnostic treatment (e.g. during diagnostic workup if a condition is suspected), as well as the prophylactic treatment (by which we include preventing and/or abrogating deterioration and/or worsening of a condition) of IPF.

'Patients' include mammalian (particularly human) patients. Human patients include adult patients.

Although, as stated above, it is preferred that C21 is employed as a first-line and/or stand-alone treatment of IPF, relevant active ingredients that may be used in combination therapy with C21 in the treatment IPF include, for example, antifibrotics (e.g. nintedanib and pirfenidone); anti-tussive drugs (e.g. dextromethorphan, codeine), glucocorticoids (e.g. beclomethasone, betamethasone, budesonide, cortisone, dexamethasone, hydrocortisone, methylprednisolone, prednisolone, prednisone and triamcinolone); PRM-151/Pentraxin-2 (Genentech/Roche); pamrevlumab (FibroGen); the galectin-3 inhibitor GB0139 (Galecto); the c-Jun N-terminal kinase inhibitor CC-90001 (Bristol Myers Squibb); the phosphodiesterase 4b inhibitor B11015550 (Boehringer Ingelheim); xylocaine; inhaled nitric oxide; immunomodulatory imide drugs (IMIDs; e.g. lenalidomide, pomalidomide and, particularly, thalidomide); other immunosuppressants, such as azathioprine and mycophenolate mofetil; vitamins (e.g. vitamin B, C and D); mucolytics (e.g. acetylcysteine and ambroxol); inflammation suppressants, such as cyclophosphamide; other immunosuppressants, such as azathioprine and mycophenolate mofetil; and antioxidants, such as N-acetylcysteine.

Relevant patients may also (and/or may already) be receiving one or more of any of the treatments and/or other therapeutic agents mentioned above for the relevant condition based upon administration of one or more of such active ingredients, by which we mean receiving a prescribed dose of one or more of those active ingredients mentioned herein, prior to, in addition to, and/or following, treatment with C21 or a salt thereof.

Pharmaceutically-acceptable salts, and doses, of other active ingredients mentioned above include those that are known in the art and described for the drugs in question to in the medical literature, such as Martindale—The Complete Drug Reference, 38th Edition, Pharmaceutical Press, London (2014 and the documents referred to therein, the relevant disclosures in all of which documents are hereby incorporated by reference.

According to two further aspects of the invention there are provided:

C21, or a pharmaceutically-acceptable salt thereof for use in; and the use of C21, or a pharmaceutically-acceptable salt thereof, for the manufacture of a medicament for any method of the invention, that is improving/restoring lung function in a patient having IPF as hereinbefore described, which treatment comprises perorally administering a therapeutically-effective amount of said C21 or salt thereof to a patient, in any manner described hereinbefore.

The uses/methods described herein may otherwise have the advantage that, in the treatment of IPF, they may be more convenient for the physician and/or patient than, be more efficacious than, be less toxic than, have a broader range of activity than, be more potent than, produce fewer side effects than, or that it may have other useful pharmacological properties over, similar methods (treatments) known in the prior art, whether used in that condition or otherwise.

Wherever the word 'about' is employed herein, for example in the context of numbers or amounts, i.e. absolute amounts such as sizes (e.g. particle sizes), volumes, doses, weights or concentrations of (e.g. active) ingredients, ages, temperatures or time periods; or relative amounts including percentages and standard deviations, it will be appreciated that such variables are approximate and as such may vary by ±10%, for example ±5% and preferably ±2% (e.g. ±1%) from the actual numbers specified. In this respect, the term 'about 10%' means e.g. ±10% about the number 10, i.e. between 9% and 11%.

EXAMPLES

The invention is illustrated, but in no way limited, by the following examples.

Example 1—Dosage Form

An excipient blend was prepared by weighing 21.4 g of colloidal silicon dioxide (AEROSIL®; Evonik) into a weighing boat. 2033.8 g of mannitol (PEARLITOL®50C, Roquette) was then weighed and approximately half of that amount was poured into to a 25L V-shell of a V-blender (Multiblender, Pharmatech, UK). The weighed amount of colloidal silicon dioxide was then added to the V-shell, followed by the remaining mannitol. The resultant mixture was blended for 10 minutes at 30 rpm.

The excipient blend was then sieved through an 800 μm sieve, prior to blending for a further 20 minutes at 30 rpm.

Half of the resultant excipient blend was weighed and re-added to the V-shell. 528 g of C21 sodium salt (Ardena, Riga, Latvia) was then added to the V-shell. The remaining excipient blend was then added to the V-shell, followed by blending for 10 minutes at 30 rpm.

The resultant blend was then sieved through an 800 μm sieve, followed by blending for 20 minutes at 30 rpm.

After the blend was prepared, blend uniformity was determined by weighing about 270 mg of blend sample into a 100 mL volumetric flask, adding 40 mL of MilliQ water and 20 minutes of sonication, adding 40 mL of methanol and sonicating for a further 20 minutes. After equilibrating to room temperature, 1.0 mL of the sample solution was added to a 10 mL volumetric flask. This was followed by diluting to the desired volume with methanol and mixing.

The sample was filtered through a 0.45 μm PTFE membrane syringe filter, and the first 3 mL of the filtrate were discarded. The amount of C21 sodium salt was determined by UHPLC. The resulting solution should contain 0.1 mg/mL of C21 Na-salt (for 100% of the nominal sample concentration).

The results are shown in Table 1 below.

TABLE 1

| Sample | Assay (%, I.c.) |
|---|---|
| 1 | 100.3 |
| 2 | 102.1 |
| 3 | 104.1 |
| 4 | 100.9 |
| 5 | 98.7 |
| 6 | 99.3 |
| Mean | 100.9 |
| RSD | 1.9 |

After this, 26.1 g of magnesium stearate (LIGAMED® MF-2-V, Peter Greven, Germany) was sieved through an 800 μm sieve and added to the blend, following by final blending for 15 minutes at 15 rpm.

The final composition is as set out in Table 2 below.

TABLE 2

| | Composition | |
|---|---|---|
| Ingredient | mg/capsule | % w/w |
| C21 sodium salt | 52.3 | 20.24 |
| mannitol (Pearlitol 50 C) | 203.38 | 77.93 |
| colloidal silicon dioxide (Aerosil 200) | 2.14 | 0.82 |
| magnesium stearate (Ligamed MF-2-V) | 2.61 | 1.00 |

Approximately 6,700 capsules were encapsulated using an MG Compact (MG2, Bologna, Italy) with dosators Size 0, in which the following settings were applied chamber— 11 mm; compression—0 mm; powder layer: 30.0 mm.

Weight sorting was done applying a 5% tolerance limit on the net fill weight of a capsule and was found to be 18.6%. After encapsulation the capsules were manually primary packaged in 100 mL high density polyethylene (HDPE) jars with child-resistant, tamper evident caps containing desiccant (56 capsules/jar).

Such capsules may also be enterically-coated.

The above process was later scaled up, such that a total of 2000 jars were produced and labelled for use in the clinical trial described in Example 2 below.

Example 2—Clinical Trial Evaluating Safety and Efficacy of C21 in Patients with IPF We report below results that have been obtained in an ongoing Phase II, multi-centre, open-label, single-arm trial investigating the safety, efficacy and pharmacokinetics of C21 in subjects with IPF.

The study is in the process of being conducted at multiple sites in India, Russia, Ukraine and the United Kingdom (UK).

The primary objective of the study is/was to investigate the safety of C21, 200 mg daily dose (100 mg b.i.d.) administered orally to subjects with IPF. The secondary objectives are/were to evaluate the effect on lung function decline of C21 and the pharmacokinetics of C21 at the same daily dose. Exploratory objectives include the investigation of a range of laboratory parameters as potential biomarkers of inflammation and fibrosis.

The primary endpoint of the trial is the nature and frequency of adverse events occurring over the trial period.

Secondary endpoints included changes from baseline in:
FVC (defined as the maximum amount of air that can be forcibly exhaled from the lungs after fully inhaling) at Weeks 12, 24 and 36;
plasma concentration of C21 and derived PK parameters evaluated in a sub-set of subjects.

Blood samples have been saved for potential future analyses of biomarkers reflecting inflammation and lung injury.

At the outset, the intention was to conduct the trial in 60 IPF antifibrotic naïve patients, but as the trial progressed the patient population was extended to include in patients who had discontinued other IPF drugs (i.e. the antifibrotic drugs mentioned above) after less than 6 months of treatment due to intolerance (with reference to Exclusion Criterion No. 18 as listed below).

IPF patients have been (and continue to be) evaluated for eligibility during a screening visit (Visit 1) and a baseline visit (Visit 2) prior to enrollment into the trial. During the eligibility evaluation it has been (and will continuing to be) checked if the patient fits all inclusion and none of the exclusion criteria.

Eligible patients have been and will be enrolled to receive daily treatment for up to 36 weeks with 200 mg C21 (100 mg b.i.d.).

Inclusion criteria include the following:
1) Written informed consent, consistent with ICH GCP R2 and local laws, obtained before the initiation of any trial related procedure.
2) A diagnosis of IPF within 5 years prior to Visit 1, as per either ATS/ERS/JRS/ATLAT/Fleischner guidelines.
3) Age ≥40 years.
4) FVC ≥60% predicted at Visit 1 and 2 (Specific for UK: FVC ≥30% predicted at Visit 1 and 2 or FVC >60% predicted at Visit 1 and 2 for subjects previously treated with antifibrotic treatment e.g. nintedanib and/or pirfenidone, or refused such treatments).
5) FEV1/FVC ratio ≥0.7 prebronchodilator at Visit 1 and 2.
6) Oxygen saturation ($SpO_2$)>85% by pulse oximetry while breathing ambient air at rest at Visit 1.
7) High-resolution computed tomography (HRCT) within 36 months prior to Visit 1 with central reading demonstrating either a or b, and c:
   a. A pattern consistent with usual interstitial pneumonitis (UIP) according to ATS/ERS/JRS/ALAT or Fleischner guidelines (Raghu et al, *Am J Respir Crit Care Med*, 198, e44 (2018); Lynch et al, *Lancet Respir Med*, 6, 138 (2018)):
      i. UIP; or
      ii. probable UIP.
   b. A pattern indeterminate for UIP according to either ATS/ERS/JRS/ALAT or Fleischner guidelines (see above) and a historical biopsy consistent with IPF.
   c. Extent of fibrosis >extent of emphysema.
8) Fully vaccinated against COVID-19 prior to screening (Visit 1). Subjects are being considered fully vaccinated for COVID-19≥14 days after they have received vaccination dose(s) according to local label.

Exclusion criteria at the outset include one or more of the following:

1) Previous use of antifibrotic treatment for an interstitial lung disease (e.g. nintedanib or pirfenidone) for >6 months.
2) Smoking (including e-cigarettes) within 6 months prior to Visit 1.
3) Body mass index (BMI)>35 or <18.
4) IPF exacerbation within 3 months prior to Visit 1 (as defined by Collard et al, *Am J Respir Crit Care Med,* 194, 265 (2016)), as defined by:
   acute worsening or development of dyspnoea typically <1 month duration;
   computed tomography with new bilateral ground-glass opacity and/or consolidation superimposed on a background pattern consistent with usual interstitial pneumonia pattern (if no previous computed tomography is available, the qualifier "new" can be dropped); or
   deterioration not fully explained by cardiac failure or fluid overload.
5) Concurrent serious medical condition with special attention to cardiac or ophthalmic conditions (e.g. contraindications to cataract surgery), or moderate to severe hepatic impairment, which in the opinion of the investigator makes the subject inappropriate for this trial.
6) Malignancy within the past 5 years with the exception of in situ removal of basal cell carcinoma and cervical intraepithelial neoplasia grade I.
7) Treatment with any of the medications listed below within 4 weeks prior to Visit 1:
   strong CYP3A4 inducers (e.g. rifampicin, phenytoin, St. John's Wort);
   strong CYP3A4 inhibitors (e.g. clarithromycin, ketoconazole, nefazodone, itraconazole, ritonavir);
   medicines that are substrates of CYP1A2, CYP3A4 or CYP2C9 with a narrow therapeutic range;
   experimental drugs;
   antifibrotic treatments; and
   any systemic immunosuppressive therapies other than:
      inhaled corticosteroids which can be used throughout the trial period provided the dose is kept stable;
      corticosteroids for the treatment of acute exacerbations; or
      the continuation of a stable daily dose of ≤15 mg prednisolone, or equivalent.
8) Treatment with any of the medications listed below within 2 weeks prior to Visit 1:
   proton pump inhibitors (PPIs) more than once daily;
   histamine H2 receptor antagonists (H2RAs);
   sulphasalazine and rosuvastatin; and
   high dose breast cancer resistance protein sensitive substrates (other than sulphasalazine or rosuvastatin).
9) Any of the following findings at Visit 1:
   prolonged QTcF (QT interval with Fridericia's correction) (>450 ms), clinically significant cardiac arrhythmias or any other clinically significant abnormalities in the resting ECG, as judged by the investigator;
   increased AST or ALT >3 times Upper Limit of Normal (ULN), or bilirubin >1.5 times ULN;
   positive results for hepatitis B surface antigen (HBsAg), hepatitis C virus antibody (HCVAb) or human immunodeficiency virus 1+2 antigen/antibody (HIV 1+2 Ag/Ab); and
   positive serum pregnancy test (minimum sensitivity 25 IU/L or equivalent units of human chorionic gonadotropin [HCG]).
10) Inability to generate lung function data at Visit 1 meeting the minimum standards of the ATS/ERS 2005 guideline (Miller et al, *Eur Respir J,* 26, 319 (2005)), as determined by central review.
11) Clinically significant abnormal laboratory value at Visit 1 indicating a potential risk for the subject if enrolled in the trial as evaluated by the investigator.
12) Pregnant or breast-feeding female subjects.
13) Female subjects of childbearing potential not willing to use contraceptive methods.
14) Male subjects not willing to use contraceptive methods.
15) Subjects not willing to adhere to dietary restrictions during the trial period.
16) Participation in any other interventional trial during the trial period.
17) Subjects known or suspected of not being able to comply with this trial protocol (e.g. due to alcoholism, drug dependency or psychological disorder).
18) Discontinuation or change of previous antifibrotic treatment (e.g. nintedanib or pirfenidone) due to disease progression.

After completion of each 12-week treatment period, the investigator made and will make a medical evaluation and decide if the subject may continue into the next 12-week treatment period. This decision is based on:
   no immediate need for other antifibrotics; and
   a positive risk/benefit balance
Failure to pass the medical evaluation results in the subject being withdrawn from the trial.

Criteria for trial withdrawal were established if any of the following occur:
   a decline from baseline in FVC value of >10% predicted on 2 consecutive occasions and an FVC <60% predicted (Specific for UK: FVC <80% predicted; or FVC <60% predicted for subjects previously treated with nintedanib and/or pirfenidone, or refused such treatments);
   a decline from baseline in FVC value of 5-10% predicted on 2 consecutive occasions and worsening of respiratory symptoms and FVC <60% predicted (Specific for UK: FVC <80% predicted; or FVC <60% predicted for subjects previously treated with nintedanib and/or pirfenidone, or refused such treatments);
   consistent failure to comply with dietary requirements, according to the investigators;
   the investigator judges it necessary due to medical reasons;
   failure to pass the medical evaluation after each 12-week treatment period;
   it is the wish of the subject to withdraw for any reason; or pregnancy.

C21 in the form of the sodium salt has been delivered as 50 mg capsules obtained according to Example 1 above.

Capsules have been packed into plastic container units with 56 capsules in each. Each unit contains either C21 or matching placebo (the same composition except that C21 has been replaced by mannitol).

At the trial site, C21 has been stored separately from normal clinic stocks in a securely locked area accessible only to authorized trial personnel. Labeling of the C21 is in the relevant local language (English), in compliance with GMP and local regulatory requirements.

C21 has been administered twice daily to the subjects for 36 weeks as follows:
   morning dose: two 50 mg capsules (100 mg C21 or placebo) to be taken with a glass of water after minimum 2 hours fasting; and afternoon/evening dose: two 50 mg capsules (100 mg C21 or placebo) to be taken with a glass of water after minimum 2 hours fasting.

Subjects are required not to eat anything for 1 hour after taking the study drug.

Clinical sites in India, Russia, Ukraine and the UK have been requested to follow the clinical trial protocol. Deviations from the protocol are recorded as protocol deviations.

Following an analysis of the results reported below and the recorded protocol deviations, it has been confirmed that all such data collected from enlisted patients regarding safety and efficacy of C21, when considered individually or as part of a cohort, is valid.

Results

A total of 21 subjects with a diagnosis of IPF (as confirmed by high-resolution computed tomography central reading) were included in an ad hoc interim analysis as described below, of which 13, 9 and 7 patients had reached 12, 24 and 36 weeks of C21 treatment, respectively.

The patients were enrolled to receive C21 (100 mg b.i.d.) for 36 weeks in total. The age and sex of the treated and evaluable subjects were characteristic of patients with IPF.

Figure 1:
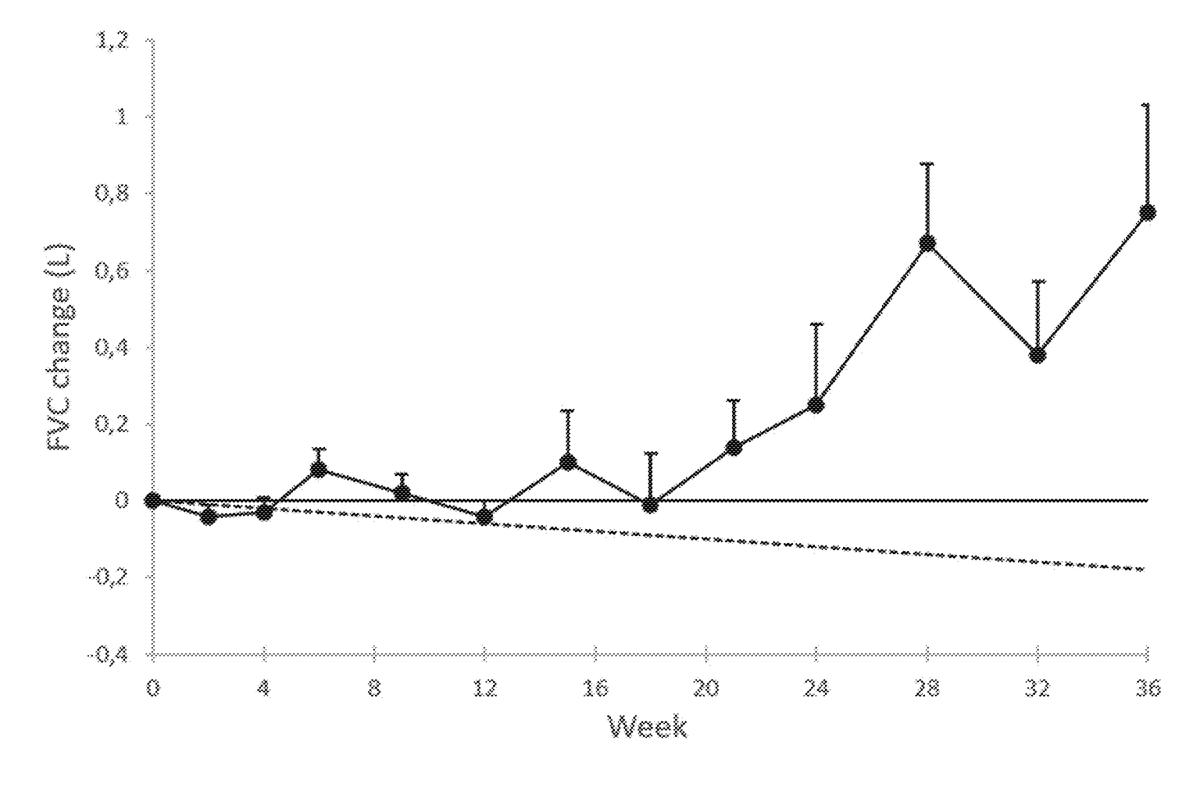
FIG. 1 shows the mean change in FVC over time (weeks) in IPF patients treated orally with 100 mg of C21 twice daily, as compared to expected FVC decline in an untreated IPF population.

As shown in FIG. 1 (observed data), after an initial stabilization of FVC, the mean FVC had increased by +250 mL at 24 weeks (solid line with circles) which, compared to the expected (based on several previously published IPF trials) mean decline of −120 mL in 24 weeks in untreated patients (dashed line), is a +371 mL difference.

At 36 weeks, the mean FVC had increased by +750 mL (solid line with circles), which, compared to the expected mean decline of −180 mL in 36 weeks in untreated patients (dashed line), is a striking +930 mL difference. Slope values (analysis of change in FVC scaled to 24 weeks, by visit, observed cases) were statistically significant at week 28 (p=0.012), week 32 (p=0.032) and week 36 ((p=0.016) versus the expected mean in untreated patients.

There were no related serious adverse events, no gastrointestinal signals and overall, no safety profile concerns. There was 1 death in the ongoing trial which was reported to be due to COVID-19 and not related to C21.

The invention claimed is:

1. A method of improving lung function in a patient having idiopathic pulmonary fibrosis which comprises perorally administering to said patient at least 2 hours after eating a therapeutically-effective amount of a sodium salt of N-butyloxycarbonyl-3-(4-imidazol-1-ylmethylphenyl)-5-iso-butylthiophene-2-sulfonamide, in the form of a powder mixture in which said salt is homogenously dispersed throughout a carrier material.

2. The method as claimed in claim 1, wherein the improvement in lung function comprises a restorative, a therapeutic, and/or a curative treatment of said idiopathic pulmonary fibrosis.

3. The method as claimed in claim 1, wherein the treatment results in at least partial restoration of lung function compared to the patient's corresponding lung function prior to said perorally administering.

4. The method as claimed in claim 1, wherein said perorally administering is carried out in the absence of co-therapy with antifibrotic drugs.

5. The method as claimed in claim 1, wherein the improvement in lung function results in one or more of the group: improved breathing, improved or restored lung ventilation, improved or restored ventilatory lung function, and increased or restored vital capacity, in the patient.

6. The method as claimed in claim 1, wherein the improvement in lung function results in the prevention of acute exacerbations of idiopathic pulmonary fibrosis.

7. The method as claimed in claim 1, wherein the improvement in lung function occurs in the significant absence of drug-related adverse events.

8. The method as claimed in claim 1, wherein the powder mixture is provided in a dosage form comprising a tablet or a capsule.

9. The method as claimed in claim 8, wherein the dosage form is a hard-shell, two-piece capsule containing the powder mixture.

10. The method as claimed in claim 8, wherein the sodium salt of N-butyloxycarbonyl-3-(4-imidazol-1-ylmethylphenyl)-5-iso-butylthiophene-2-sulfonamide is provided in the form of particles in the powder mixture, the particles having a weight-based mean diameter as measured by sieving and/or a volume-based mean diameter as measured by laser diffraction that is no more than about 50 μm.

11. The method as claimed in claim 8, wherein the carrier material comprises carrier particles with a weight-based mean diameter as measured by sieving that is no more than about 400 μm.

12. The method as claimed in claim 11, wherein the weight-based mean diameter of the carrier particles is no more than about 200 μm.

13. The method as claimed in claim 11, wherein the weight-based mean diameter of the carrier particles is between about 50 μm and about 100 μm.

14. The method as claimed in claim 11, wherein the carrier particles comprise mannitol.

15. The method as claimed in claim 8, wherein the dosage form comprises an enteric coating.

16. The method as claimed in claim 15, wherein the enteric coating comprises polyvinyl acetate phthalate or a methacrylic acid copolymer.

17. The method as claimed in claim 8, wherein the dosage form is essentially water-free.

18. The method as claimed in claim 1, wherein said patient having idiopathic pulmonary fibrosis has probable usual interstitial pneumonitis.

19. The method as claimed in claim 18, wherein probable usual interstitial pneumonitis is determined by a pattern on a high-resolution computed tomography image.

* * * * *

UNITED STATES PATENT AND TRADEMARK OFFICE
CERTIFICATE OF CORRECTION

PATENT NO. : 11,819,494 B2
APPLICATION NO. : 17/680654
DATED : November 21, 2023
INVENTOR(S) : Dalsgaard and Batta It is certified that error appears in the above-identified patent and that said Letters Patent is hereby corrected as shown below:

In the Claims

In Claim 1, at Column 27, Line 49, after "material" and before the ".", insert:
--, wherein said perorally administering is effective to improve lung function in the patient--

Signed and Sealed this
Thirteenth Day of February, 2024

Katherine Kelly Vidal
*Director of the United States Patent and Trademark Office*